(12) United States Patent (10) Patent No.: US 8,715,301 B2
Domingo (45) Date of Patent: May 6, 2014

(54) ARTHROSCOPIC SOFT TISSUE PLICATION SYSTEMS AND METHODS

(75) Inventor: Nicanor A. Domingo, Santa Clara, CA (US)

(73) Assignee: Cayenne Medical, Inc., Scottsdale, AZ (US)

( * ) Notice: Subject to any disclaimer, the term of this patent is extended or adjusted under 35 U.S.C. 154(b) by 1275 days.

(21) Appl. No.: 11/850,614

(22) Filed: Sep. 5, 2007

(65) Prior Publication Data

US 2008/0077162 A1 Mar. 27, 2008

Related U.S. Application Data

(60) Provisional application No. 60/842,217, filed on Sep. 5, 2006, provisional application No. 60/931,354, filed on May 22, 2007.

(51) Int. Cl.
*A61B 17/04* (2006.01)

(52) U.S. Cl.
USPC .......................................... 606/144; 606/139

(58) Field of Classification Search
USPC ......................................... 606/139, 144–147
See application file for complete search history.

(56) References Cited

U.S. PATENT DOCUMENTS

| | | | |
|---|---|---|---|
| 5,015,249 A | 5/1991 | Nakao et al. | |
| 5,059,201 A * | 10/1991 | Asnis ............................ | 606/144 |
| 5,336,231 A | 8/1994 | Adair | |
| 5,403,326 A | 4/1995 | Harrison et al. | |
| 5,431,666 A | 7/1995 | Sauer et al. | |
| 6,533,795 B1 | 3/2003 | Tran et al. | |
| 6,551,330 B1 | 4/2003 | Bain et al. | |
| 6,618,626 B2 | 9/2003 | West et al. | |
| 6,770,084 B1 | 8/2004 | Bain et al. | |
| 6,893,448 B2 | 5/2005 | O'Quinn et al. | |
| 6,921,361 B2 | 7/2005 | Suzuki et al. | |
| 7,063,715 B2 * | 6/2006 | Onuki et al. .................. | 606/220 |
| 7,112,208 B2 | 9/2006 | Morris et al. | |

(Continued)

FOREIGN PATENT DOCUMENTS

| | | |
|---|---|---|
| WO | 9627331 A1 | 9/1996 |
| WO | 9903402 A1 | 1/1999 |
| WO | 0189370 A2 | 11/2001 |
| WO | 2008113076 A2 | 9/2008 |
| WO | 2009005527 A1 | 1/2009 |

OTHER PUBLICATIONS

International Search Report, Jul. 25, 2008, corresponding to PCT Application No. PCT/US07/77664; Written Opinion of International Searching Authority, Jul. 25, 2008, corresponding to PCT Application No. PCT/US07/77664.

*Primary Examiner* — Gregory Anderson
(74) *Attorney, Agent, or Firm* — Stout, Uxa, Buyan & Mullins, LLP; Donald E. Stout

(57) ABSTRACT

A system and method for repairing soft tissue comprises introducing an instrument having a shaft into an operative site, such as a human shoulder. Then, a flexible grasper is advanced from the instrument to capture a portion of soft tissue. The flexible grasper is then retracted so that the captured tissue lies in a pathway for a needle in the instrument. The needle is advanced along the pathway through the captured tissue, and then a portion of suture is captured with the needle, distally of the captured tissue. The needle is retracted proximally through the captured tissue, to thereby pass the suture therethrough and plicate the tissue. The plicated tissue is then released from the grasper.

17 Claims, 12 Drawing Sheets

(56) References Cited

U.S. PATENT DOCUMENTS

| | | |
|---|---|---|
| 7,166,116 B2 | 1/2007 | Lizardi et al. |
| 2002/0128533 A1 | 9/2002 | Barker |
| 2003/0120289 A1* | 6/2003 | McGuckin et al. ........... 606/151 |
| 2003/0236535 A1* | 12/2003 | Onuki et al. ................. 606/144 |
| 2004/0034371 A1 | 2/2004 | Lehman et al. |
| 2004/0059352 A1 | 3/2004 | Burbank et al. |
| 2004/0092968 A1 | 5/2004 | Caro et al. |
| 2008/0077162 A1 | 3/2008 | Domingo |

* cited by examiner

ARTHROSCOPIC SOFT TISSUE PLICATION SYSTEMS AND METHODS

This application claims the benefit under 35 U.S.C. 119(e) of the filing date of Provisional U.S. Application Ser. No. 60/842,217, entitled Arthroscopic Soft Tissue Plication Systems and Methods, filed on Sep. 5, 2006, and of the filing date of Provisional U.S. Application Ser. No. 60/931,354, entitled Arthroscopic Soft Tissue Plication System, filed on May 22, 2007. Both of these prior provisional applications are expressly incorporated herein by reference.

This application is also related to co-pending U.S. application Ser. No. 11/045,209, entitled Devices, Systems, and Methods for Tissue Repair, filed on Jan. 31, 2005 and published as U.S. Patent Application Publication No. US 2005/0267529 on Dec. 1, 2005, which application is commonly owned and herein expressly incorporated by reference.

BACKGROUND OF THE INVENTION

This invention relates generally to methods and apparatus for repairing soft tissue arthroscopically, and more particularly to methods and apparatus for surgically stabilizing a human shoulder joint. Specifically, the present invention involves unique arthroscopic handheld devices, systems, and methods for grasping and subsequently tightening the should capsule via suture plication.

Tissue instability or compromise is a common occurrence in all persons, whether induced by age, repeated use, disease, accident, or natural and abnormal formation. Such instability may include, for example, intentional or accidental tears, cuts, stretching, loosening, deterioration of structure, loss of firmness, and the like. Furthermore, such tissue may relate to orthopedics, as in the skeletal system and its associated muscles, joints and ligaments and the like, or non-orthopedic systems, such as smooth muscles, gastrointestinal, cardiac, pulmonary, neural, dermal, ocular and the like.

No matter what type of instability is present or whether the tissue to be repaired is classified as orthopedic or non-orthopedic, similar issues and objectives are encountered by the surgeon, namely, creating a stable and reliable structure and doing so in as easy and reliable manner as possible. For example, a neurosurgeon aims to create a stable and reliable adhesion of two neural tissue structures, while at the same time creating minimal damage. The neurosurgeon desires a technique that is minimally invasive, highly reproducible, and reliable, and highly effective in connecting the tissue to itself or other similar or dissimilar tissue. It would be even more beneficial to somehow have the tissue become induced to adhere to itself or the other tissue.

In another similar example, in orthopedics soft tissue surgery, the surgeon desires to repair the damaged or diseased tissue in such a manner that the tissue binds with itself or other tissue in a firm but minimally damaging manner. In muscle or ligament repair, for example, it is necessary to suture the tissue together to promote strength and unity in the structure while at the same time, allow for natural movement to occur.

More broadly, traditional soft tissue repair is a common procedure that typically involves some form of conventional suturing or stapling. For example, certain joints, such as hips, knees, shoulders, and elbows contain tissues that are common sources of problems, whether natural or induced, that require extensive physical therapy or surgery to correct. There are similarities between such examples of tissues that present a uniform set of issues for the health care worker such that a treatment of one type of tissue will be in many ways similar to the treatment of another type of tissue, even though the shape, properties and architecture of each tissue is uniquely different. Of such tissues or tissue structures, a common source of medical problems occurs in the joints. Although the below example will be described with respect to the shoulder joint, similar problems are inherent in other soft tissue areas and one having ordinary skill in the art would be cognizant of such problems and how to apply the principles of the present invention to address the problems in such other tissues or tissue systems.

Joint instability is a complex clinical problem associated with a variety of treatment options that include the use of arthroscopic and open surgical methods. For example, for the shoulder joint, open surgical methods for producing a capsular shift to increase the capsular ligament tension and improve the joint stability have been demonstrated. However, adequate arthroscopic methods that approximate the clinical outcome achieved by open surgical methods for reducing excessive joint laxity have been slow to develop or have begun to show less than optimal long term clinical outcomes (e.g. thermal methods).

The shoulder joint, in particular, has inherent instability because of its large range of motion combined with the relatively shallow joint bony socket (glenoid). Anatomically, the rotator cuff acts as the primary dynamic joint stabilizer, while the inferior glenohumeral ligament acts as the primary static shoulder joint stabilizer. Damage to or laxity of one of these stabilizing structures can result in the presentation of clinically relevant shoulder instability.

The onset of shoulder instability is generally associated with a traumatic injury, an atraumatic motion injury, or chronic overuse of the shoulder. Most typically, the instability of the shoulder stems from disruption and/or looseness (excessive capsule laxity) of the shoulder capsule. The resulting subluxation or dislocation of the joint can be painful and debilitating for the individual. The overall approach of shoulder stabilization surgery is to first repair the disrupted/torn capsule and second to tighten the loose capsule ligaments. Of note, there are instances where the capsule is intact (e.g. no tear) and only tightening of the capsule ligaments is required to restore joint stability. The ultimate goals of shoulder stabilization include restoring appropriate capsule tension, limiting of humeral head translation, and excessively decreasing range of motion.

Up to 98% of all shoulder joint dislocations occur in the anterior direction, 95% of which are first time dislocations. Over 70% of these individuals will have recurrent instability (subluxation or dislocation) within two years after the first event, potentially requiring surgical intervention.

Certain conventional devices serve to assist with the repair of the shoulder capsule when it is disrupted, such as in the case of Bankart Lesions. It is noted that Bankart Lesions are identified by the characteristic stripping/tearing of the anterior inferior labrum from the glenoid. Treatment of these lesions is typically accomplished through a standard open incision or with existing arthroscopic technology.

Clinically described excess joint laxity in the joint capsule can range from 1.0 to more than 20.0 mm in ligament elongation, resulting in recurrent glenohumeral subluxation or dislocation. A loose shoulder capsule may be tightened readily when a standard open incision is used, but tightening the shoulder capsule arthroscopically poses significant challenges with existing instruments. For example, the acute angles at which the surgical devices are able to approximate the soft tissue and identify regions where suturing would be desirable are limiting. Furthermore, the ability to pass a suture and tie snug surgical knots that compress the tissue in the desired plane with a reasonable suture time is difficult if not cumbersome. Finally, the ability to dictate the level of tissue tied is limited to the tissue needle bite size and remains difficult for the surgeon to reproducibly specify the level of tissue compression desired.

A recently introduced technology, thermal capsulorrhaphy, initially held significant promise as a means of facilitating and expediting arthroscopic shoulder capsule tightening. The premise of this technique is to manipulate the characteristics of the approximately 90% Type I collagen structure of ligaments by thermal exposure. It has been demonstrated that at temperatures above 65 degrees Celsius, collagen begins to denature (e.g., unwinding of the helical structure), resulting in tissue shrinkage. Collagen shrinkage of up to 50% has been demonstrated using thermal energy. However, this technology has yielded equivocal results and progressive skepticism from shoulder surgeons. Specifically, concerns related to long term clinical outcomes for shoulder instability with altered capsular structure have been noted. There is a strong current sentiment among shoulder surgeons that tightening the shoulder capsule by plication with sutures will prove to be more efficacious and more reproducible than the use of thermal mechanisms to reduce the ligament laxity in the capsule.

Additional concerns of thermal capsulorrhaphy application include potential injury to the axillary nerve, bleeding, pain, and excessive swelling of the capsule. More importantly, the technical methods used during thermal capsulorrhaphy do not allow the surgeon to control the level of plication that is desired or anticipated. Specifically, thermal methods are technique-specific and have a required learning curve associated with obtaining specified clinical plication outcomes. Moreover, once treated, the level of resulting tissue alteration achieved is irreversible. The paucity of data demonstrating the long-term mechanical characteristics and viability of these treated ligaments limits the confident and continued use of this technique.

Conventional methods for arthroscopic plication of the shoulder capsule with sutures typically involve freehand techniques that are technically challenging and often time-consuming. An additional shortcoming common to both thermal capsular shrinkage and existing suturing techniques is that either method can effectively control the amount of capsular tightening in a calibrated fashion. Over-tightening of the anterior capsule can lead to problems such as excessive loss of external rotation, limiting shoulder joint function.

Thus, a need exists in the art for an alternative to the conventional methods of tissue repair. There is a need in the art for novel systems and methods for arthroscopic soft tissue repair and/or plication that is adaptable to any soft tissue or soft tissue system and can overcome the shortcomings of conventional methods and improve the clinical outcome as well as be generally adopted by surgeons.

SUMMARY OF THE INVENTION

The present invention provides an alternative and enhancement to conventional methods of tissue repair. More specifically, the present invention provides devices, systems, and methods for arthroscopically treating unidirectional and multidirectional instability of tissue in general, and through suturing and/or plication by non-limiting example. An important aspect of this invention is its wide applicability to a non-limiting extent of tissues and tissue systems of any shape or size, such as, for example, the plication of loose tissue from the interior surface of a spheroidal capsule. One having ordinary skill in the art is cognizant of the applicability of the present invention to as diverse fields as reduction in gastric reflux to lung volume reduction to atrial valve repair and shoulder joint plication. The present invention is not limited to the examples set forth in this disclosure, but is extended to all other procedures that would benefit from the devices, systems, and methods as described herein. Thus, the scope of the present invention extends beyond the non-limiting examples set forth herein and encompasses that which would be or should be within the purview of one having ordinary skill in the art of tissue repair.

In one aspect of the invention, there is provided a system for transdermal repair of soft tissue which includes an instrument comprising an instrument shaft having an axis. A flexible grasper is disposed within the instrument shaft and is capable of advancing and retracting in a generally axial direction. A suture source is provided, and a needle is disposed within the instrument shaft. The suture source preferably comprises a suture cartridge having a length of suture pre-loaded thereon. The suture cartridge is either re-loadable with additional lengths of suture, or replaceable with another pre-loaded suture cartridge, in order to create the next plication stitch. The needle is capable of advancing and retracting in a generally axial direction. The flexible grasper preferably comprises a flexible cable having a plurality of hinged jaws capable of articulation between closed and opened orientations on a distal end thereof. A controller is disposed on a proximal portion of the instrument for opening and closing the hinged jaws. A locking mechanism is provided for locking said grasper in one of a closed and opened orientation.

Additionally, a controller is provided on a proximal handle portion of the instrument for selectively advancing and retracting the instrument shaft. Another controller is provided for advancing and retracting said needle.

A suture pick-up feature is disposed at a distal end of the instrument, on which is disposed a portion of a length of suture. A suture hook on a distal end of the needle has a purpose of engaging and retaining the portion of a length of suture as the needle is advanced to the suture pick-up feature.

The grasper is adapted to capture a desired portion of soft tissue and to withdraw the captured portion of tissue proximally to a desired location. The desired location is in a pathway of the needle as the needle is advanced or retracted.

The instrument shaft may be selectively advanced to various distal positions in order to select a desired plication length, and may be locked into a desired advanced distal position.

Advantageously, the inventive instrument further comprises a suture relief groove and a suture path groove for providing relief space for the suture and for reducing loading forces on the needle as it passes through the captured tissue.

In another aspect of the invention, there is provided a system for transdermal repair of soft tissue, which comprises an instrument having a shaft. The instrument has an axis, and a needle is disposed on the instrument, which is capable of advancement and retraction in a generally axial direction. A needle support tube is provided which is capable of advancing and retracting in coordination with the needle. The needle support tube may have a sharpened distal tip or a blunt distal tip, and in a preferred embodiment two needle support tubes, one having a sharpened distal tip and the other having a blunt distal tip, are provided. Either of the sharpened or blunt needle support tubes may be selectively advanced to contact a portion of soft tissue captured by the instrument prior to advancement of the needle through the portion of tissue.

Additionally, the system comprises a flexible grasper disposed within the instrument shaft, which is capable of advancing and retracting in a generally axial direction, for capturing a portion of soft tissue for plication.

In still another aspect of the invention, a method of repairing soft tissue is disclosed, which comprises a step of introducing an instrument having a shaft into an operative site, such as a human shoulder. Then, a flexible grasping means is advanced from the instrument to capture a portion of soft tissue. The flexible grasping device is then retracted so that the captured tissue lies in a pathway for a needle in the instrument. The needle is advanced along the pathway through the captured tissue, and then a portion of suture is captured with the needle, distally of the captured tissue. The needle is retracted proximally through the captured tissue, to thereby pass the suture therethrough and plicate the tissue. The plicated tissue is then released from the grasper.

The aforementioned method includes a further step of advancing a needle support tube into contact with the captured tissue prior to the step of advancing the needle. The advanced needle support tube has a sharpened distal tip for penetrating the captured tissue without creating a pleat of tissue, prior to passage of the needle therethrough. Alternatively, the advanced needle support tube has a blunt distal tip for contacting the capture tissue and creating a pleat of tissue prior to passage of the needle therethrough. The instrument for performing the inventive method may include both a needle support tube having a sharpened distal end and a needle support tube having a blunt distal end, so that the practitioner may select either of the needle support tubes for advancement, depending upon the nature of the captured tissue and other factors relating to the particular plication procedure.

Preferably, the described method comprises a further step of determining a desired plication length by determining a desired suture entrance point and a desired suture exit point in the desired portion of soft tissue, and then advancing the instrument shaft to a distal location which will result in the desired suture entrance and exit points, and locking the instrument shaft in the desired distal location.

The invention, together with additional features and advantages thereof, may best be understood by reference to the following description taken in conjunction with the accompanying illustrative drawing.

DESCRIPTION OF THE PREFERRED EMBODIMENT

Figure 1:
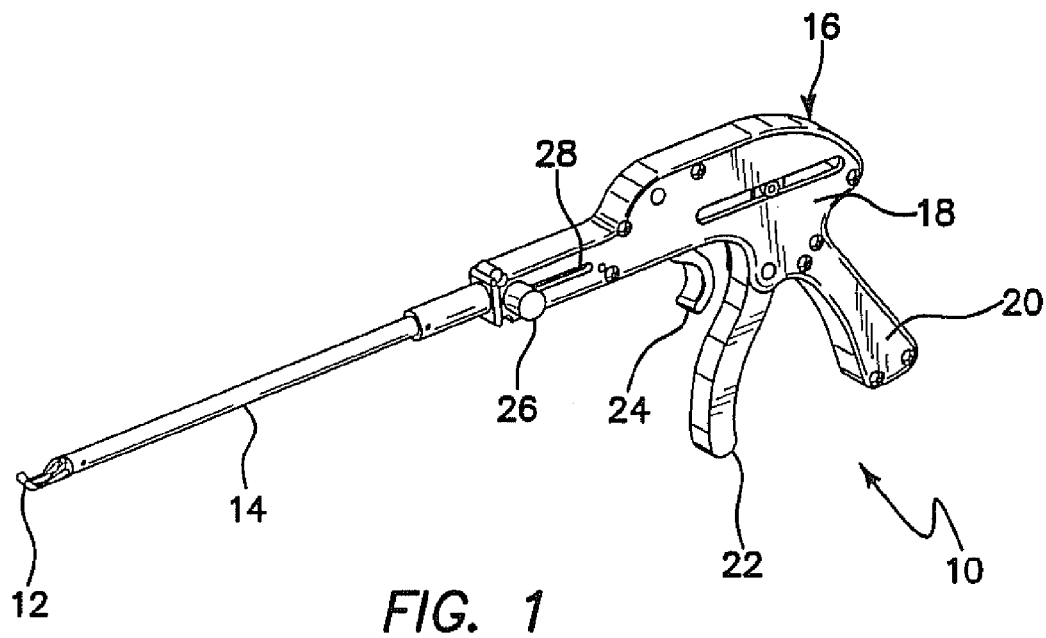
FIG. 1 is a perspective view of a plication instrument constructed in accordance with one embodiment of the present invention.

Referring now more particularly to the drawings, there is shown in FIG. 1 a plication instrument 10. The instrument 10 comprises a distally disposed suture cartridge 12 and an instrument shaft 14 extending proximally from the suture cartridge 12. A handle portion 16 comprises a handle housing 18, which is integrated into the shaft 14, as well as a grip 20, a needle advancement lever 22, and a grasper actuation trigger 24. A shaft advancement knob 26 is slidable axially within a slot 28.

The attachment of the suture cartridge 12 to the instrument shaft 14 allows the surgeon to unload and re-load suture cartridges after every plication stitch.

Figure 2:
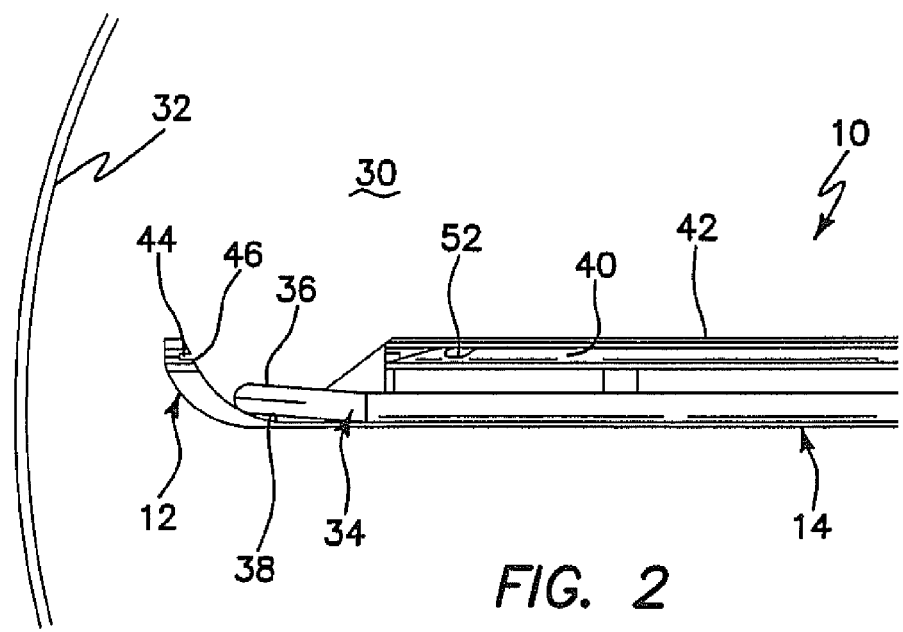
FIG. 2 is a side view of the distal working end of the instrument shown in FIG. 1, wherein the instrument has been introduced into an operative site.

Now with reference to FIG. 2, a distal end of the instrument 10 is illustrated. In this figure, the instrument 10 has been introduced into an operative site 30, which is preferably a human shoulder. Within the shoulder 30, the instrument 10 is illustrated as it approaches the shoulder capsule 32. A flexible cable grasper 34 is positioned within the instrument 10, and is equipped with hinged upper and lower jaws 36, 38, respectively at its distal end. The grasper 34 is designed to maintain a low profile within the instrument 10, for facilitating easy insertion into the cannula typically used to introduce the instrument into the operative site during arthroscopic surgery. The flexible cable grasper 34 is housed inside the instrument shaft 14 and is axially fixed to the proximal handle portion 16. The flexible cable grasper has a flexible shaft, preferably comprised of tightly coiled biocompatible metallic material, on its distal end to allow it to maneuver in and out of the instrument as the instrument shaft 14 is advanced and retracted. A needle 40 is also provided, disposed within a needle support tube 42, above the grasper 34. The needle 40 and needle support tube 42 are illustrated in a retracted position in FIG. 2, in anticipation of the grasper 34 exiting the distal end of the instrument 10. Suture 44 is loaded onto the suture cartridge 12 and is prepared to be hooked onto the needle 40 at a suture pick-up feature 46 on the suture cartridge 12.

Figure 3:
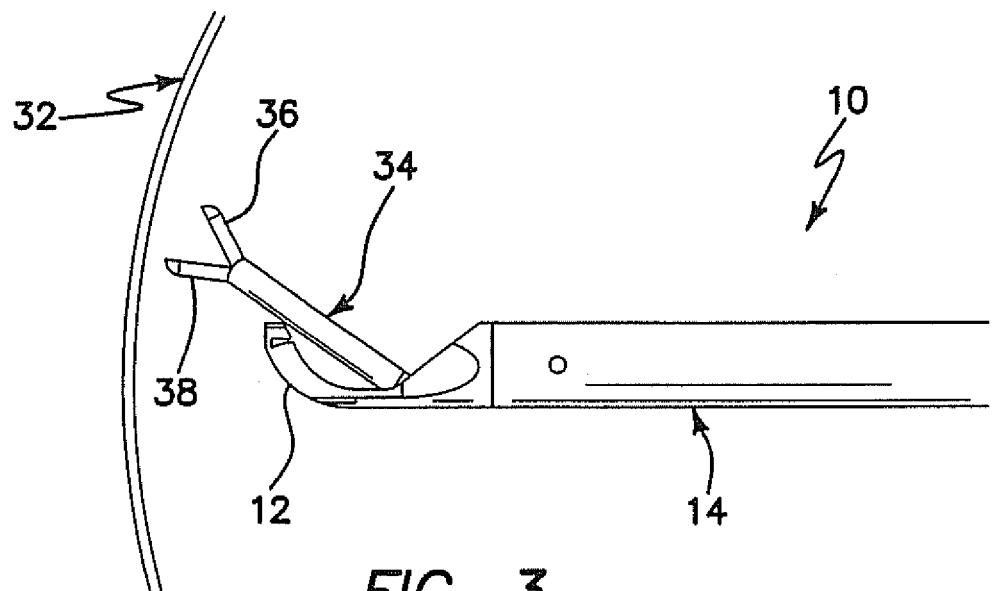
FIG. 3 is a side view similar to FIG. 2, wherein the instrument shaft is in a retracted position so that the graspers have exited the instrument.

In FIG. 3, a frontal view of the distal end of the instrument 10 is illustrated, wherein the instrument shaft 14 is in a retracted position, which results in the grasper 34 exiting the instrument and reaching target capsule tissue 32. A redirecting curve in the suture cartridge 12 guides the grasper 34 out of the instrument as the instrument shaft 14 is retracted. At this juncture, the jaws 36, 38 are actuated to an open position, as shown, by means of grasper actuation trigger 24 (FIG. 1), for an attempt to grab the target tissue 32.

Figure 4:
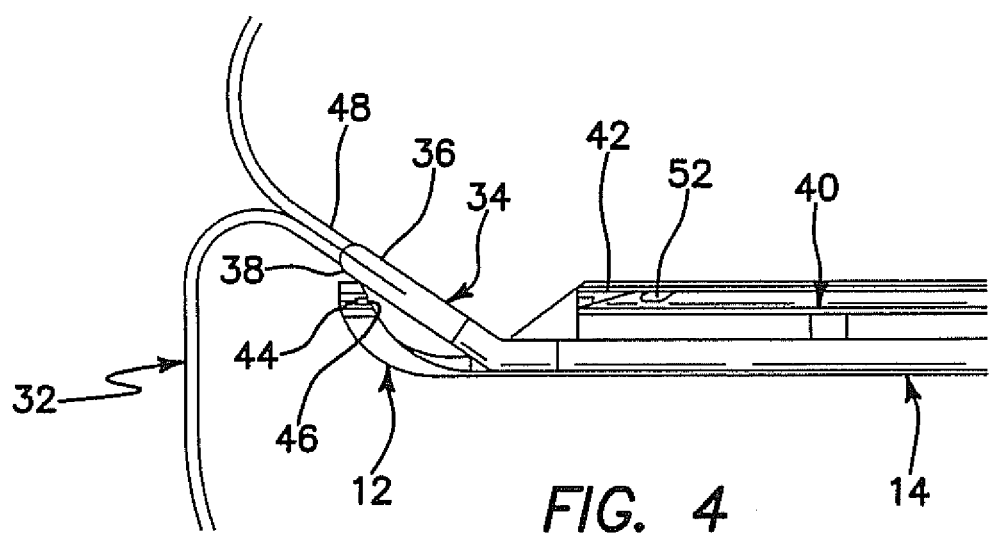
FIG. 4 is a cross-sectional view of the distal working end of the instrument of FIGS. 1-3, showing the grasper holding capsule tissue outside of the instrument.

With reference now to FIG. 4, a cross-sectional view of the distal end of the instrument is shown, wherein the grasper 34 holds a portion 48 of the target tissue 32 outside of the instrument. The needle 40 and the needle support tube 42 are still in the retracted position, waiting for the tissue portion 48 to be positioned properly in the instrument.

Figure 5:
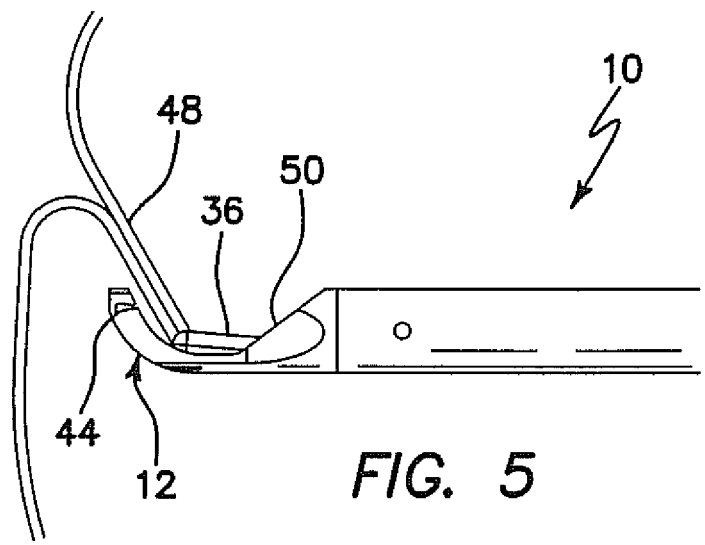
FIG. 5 is a side view similar to FIGS. 2 and 3, showing the capsule tissue in the graspers after it has been pulled into the instrument.

In FIG. 5, the captured tissue portion 48 has been pulled into a tissue receiving bowl 50 in the instrument 10. The tissue portion 48 is now positioned for plication, because it is in a direct path of the needle 40 and the needle support tube 42, as will be explained further below.

Figure 6:
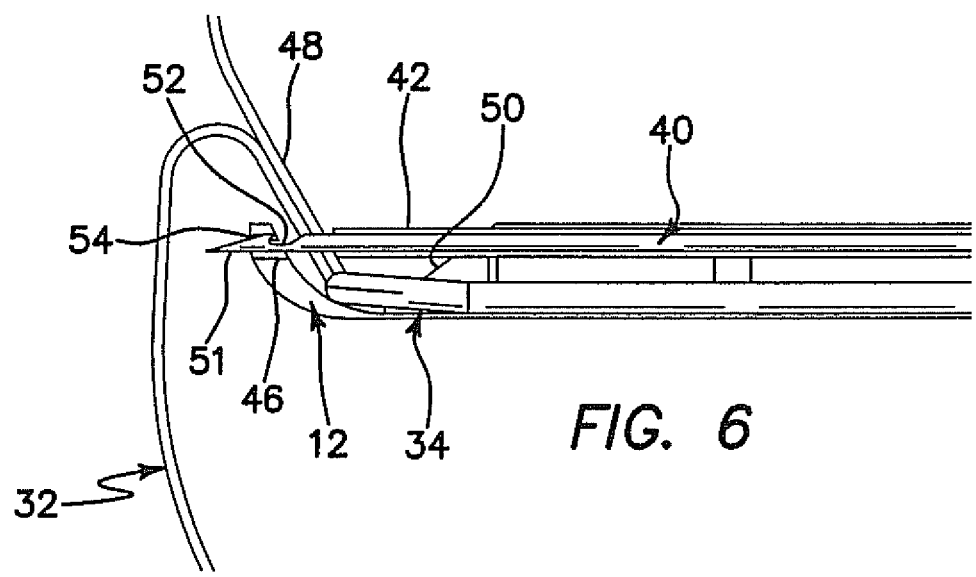
FIG. 6 is a cross-sectional view similar to FIG. 4 showing the needle piercing the capsule tissue and picking up a length of suture.

FIG. 6 is again a cross-sectional view of the distal end of the instrument, illustrating the advancement of the needle 40 so that a needle piercing tip 51 of the needle 40 pierces the tissue portion 48 and extends into the suture pick-up feature 46 of the suture cartridge 12. As is seen in FIG. 6, but also in FIGS. 2 and 4, the distal end of the needle 40 includes a needle suture hook 52. The needle suture hook 52 acts to pick up the suture 44 as the needle 40 advances into the suture pick-up feature 46. The advancement of the needle 40, as illustrated, occurs once the grasper 34 positions the tissue portion 48 in the direct path of the needle 40. However, prior to advancement of the needle 40, the needle support tube 42 is advanced in order to create a pleat in the tissue portion 48, as shown. When the needle support tube 42 reaches its final advanced position, the needle 40 advances and pierces the tissue portion 48, as shown. The needle 40 then reaches the suture 44 at the suture pick-up feature 46. The needle 40 then flexes as the needle tissue piercing tip 51 ramps under the suture 44. The needle 40 continues to advance until the needle suture hook 52 is reached and the needle 40 flexes back to an unsprung, straight condition. At this point, the suture 44 is now positioned in the needle suture hook 52 and is captured by the needle 40. The suture pick-up feature 46 of the suture cartridge 18 maintains a hold on the suture 44 during this maneuver. A slot within the needle suture hook 52 (not shown) permits the suture 44 to be positioned in the path of the needle 40 on the distal side of the pleated tissue portion 48. A hole 54 on the distal tip of the suture cartridge 12 permits the needle 40 to protrude out of the instrument, as shown, but prevents the suture 44 from following the needle 40. As the needle 40 is retracted (FIG. 7), the suture pick-up feature 46 maintains the position of the suture 44 so that the needle suture hook 52 can capture the suture 44 and retract it back through the tissue portion 48.

Figure 7:
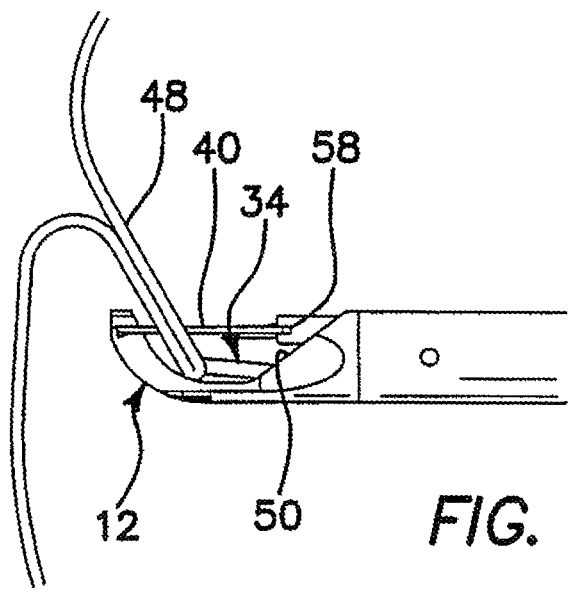
FIG. 7 is a side view similar to FIGS. 2, 3, and 5 showing the grasper maintaining a hold of the pleated capsule tissue as the needle retrieves the suture through the tissue.

In FIG. 7, it can be seen that, the grasper 34 maintains a grip on the pleated tissue portion 48 as the needle 40 retrieves the suture 44 from the suture cartridge 12 and retracts proximally back through the tissue 48. To reduce the force required to retrieve the suture-loaded needle 40 back through the tissue portion 48, needle suture channels 56 (FIG. 8) are provided in order to provide relief space for the suture 44. With the suture 44 in the needle suture channels 56, the profile of the suture-loaded needle 40 is reduced, which in turn reduces the force required to bring the needle 40 back through the tissue portion 48. A suture relief groove 58 is provided in the needle support tube 42 to also help facilitate this maneuver. The groove 58 provides a relief space for the suture 44 on the proximal side of the tissue portion 48. Another component that assists this maneuver is a needle return spring 60 (FIG. 14) located in the proximal handle housing 18. This spring 60 is compressed when the needle 40 is fully advanced, thus creating a return force for the needle to return back through the tissue portion 48 and back into the needle support tube 42.

Figure 8:
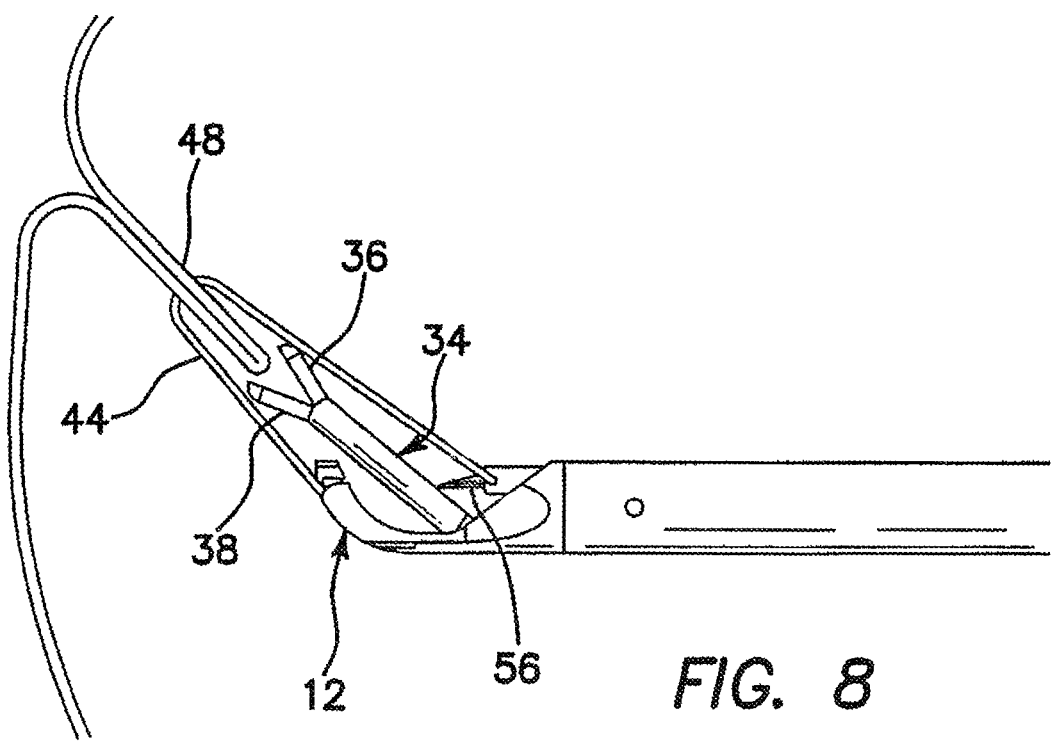
FIG. 8 is a side view similar to FIGS. 2, 3, 5 and 7 showing the grasper releasing the pleated tissue with the suture passed through it.

In FIG. 8, the grasper 34 has been actuated to an open position, so that the pleated tissue portion 48 is released, with the suture 44 passed through it, as shown. To perform this step, the instrument shaft 14 is retracted proximally, causing the flexible cable grasper 34 to exit the instrument. The grasper jaws are actuated open, thereby releasing the tissue portion 48. A suture path groove 62 (FIG. 13) in the suture cartridge 12 is designed in such a way that friction is minimized, thereby allowing the suture 44 to be dispensed out of the instrument during this maneuver and as the instrument is retracted from the pleated tissue portion 48. The spring-loaded needle 40 maintains a hold on the suture 44 during this step and the opposite end of the suture is free to be dispensed out of the instrument.

Figure 9:
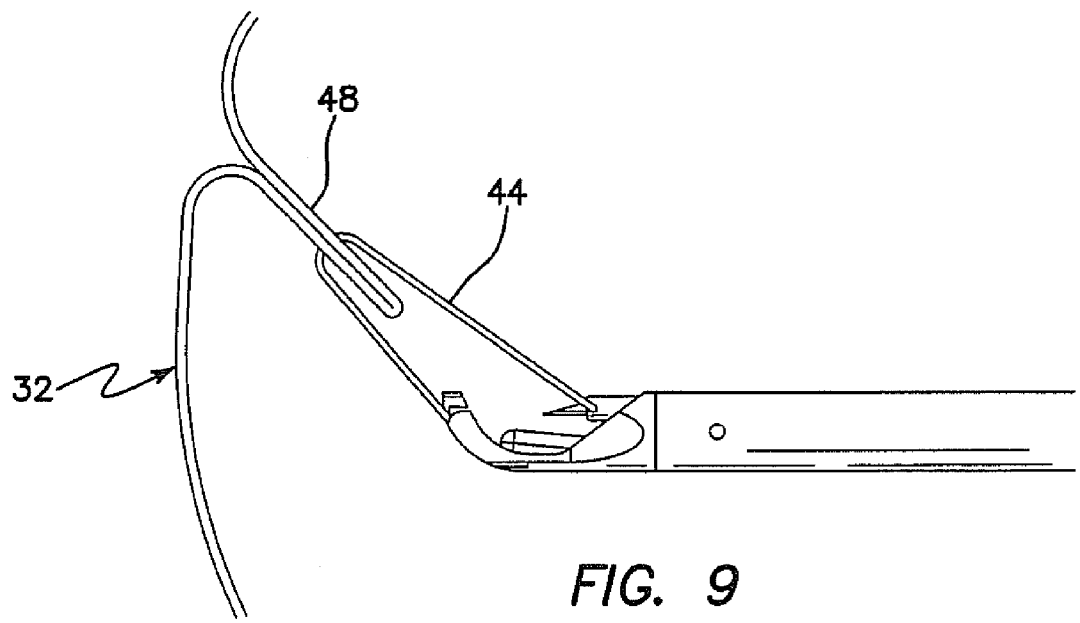
FIG. 9 is a side view similar to FIG. 8 showing the tissue completely released from the grasper.

In FIG. 9, the pleated tissue portion 48 is completely released from the grasper 34. The instrument shaft 14 is advanced, and the flexible cable grasper 34 is retracted back into the instrument. The instrument is retracted from the pleated tissue portion 48, and is removed from the operative site 30 while the suture 44 continues to be dispensed out of the instrument.

Figure 10:
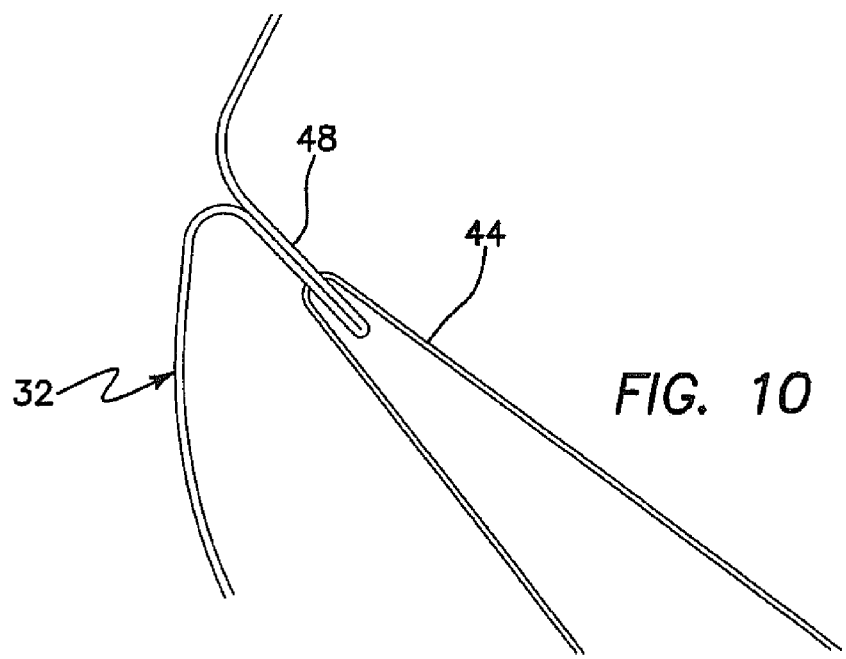
FIG. 10 is a schematic view showing the pleated tissue after the plication instrument has been withdrawn from the operative site.

FIG. 10 illustrates a completed procedure, using the instrument 10. A pleat 48 of the shoulder capsule tissue 32 has been created, and a suture loop 44 passes through the pleat 48. To complete the procedure, the surgeon now throws the appropriate standard knots in the suture, thus cinching the pleat 48, and resulting in plicated capsule tissue 32.

Figure 11:
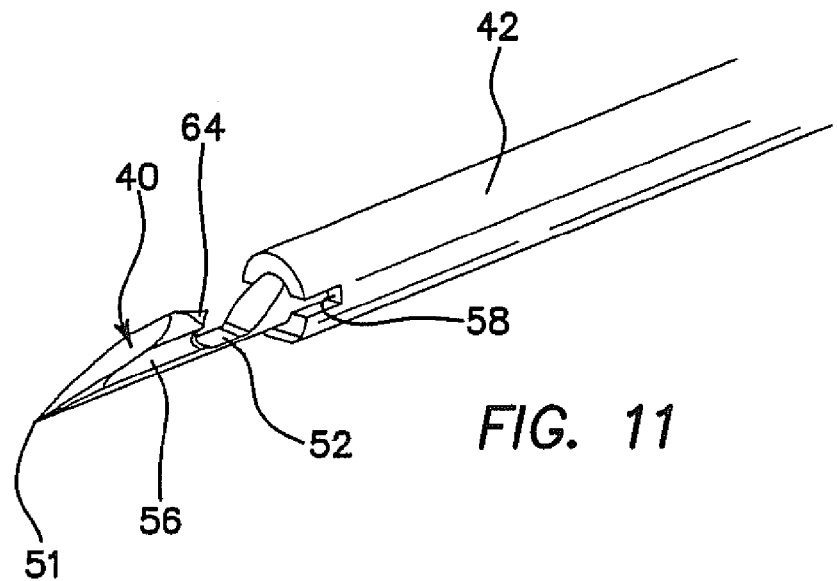
FIG. 11 is a perspective view showing the distal end of the instrument.

FIG. 11 illustrates a close-up view of the distal end of the needle 40 and needle support tube 42. The needle tissue piercing tip preferably comprises a triple bevel geometry, commonly used in hypodermic needles for piercing tissue. The suture hook 52 is the feature that captures the suture 44 during the needle retraction maneuver. The large opening on the proximal side of the hook 52 permits the suture 44 to slide in easily, and the overhang feature maintains the suture within the hook, capturing it while the needle 40 is retracted. On both sides of the needle 40, suture channels 56 are cut into the needle 40 to provide relief space for the suture 44 during the needle retraction maneuver. Also, to reduce the force required to retract the needle 40 through the tissue 48, a sharp triple bevel geometry is created on the overhang feature of the suture hook 52, resulting in a needle retraction tip 64. This needle retraction tip 64 provides a lead-in into the tissue 48 to ease the retraction maneuver and may also create a small incision through the capsule tissue 32. This creates a larger opening, which also eases the retraction maneuver. The suture relief groove 58 in the needle support tube 42 also aids the needle retraction maneuver by providing a relief space for the suture 44 on the proximal side of the tissue 48. this prevents the tissue 48 from getting caught between the suture 44 and the needle support tube 42, which would result in high needle retraction forces. The needle support tube 42 provides several functions. One function is to delay the needle 40 from piercing the tissue 40 until the target size pleat is created. Without the needle support tube 42, controlling the position where the needle pierces the tissue would be difficult. The distance between the peak of the pleat and the location where the needle pierces the tissue is the pleat length. Thus, controlling the needle piercing location also controls the length of the pleat to be plicated.

Another function of the needle support tube 42 is to provide structural support and maintain alignment of the needle 40 to the suture pick-up feature 46. During the needle piercing maneuver, lateral loads may be imposed on the needle 40 which could cause the needle 40 to flex and misalign from the suture pick-up feature 46. The needle support tube 42 extends out from the suture cartridge 12, minimizing the unsupported length of the needle 40. Yet another function of the needle support tube is to provide an opposing force against the tissue during the needle retraction maneuver.

Figure 12:
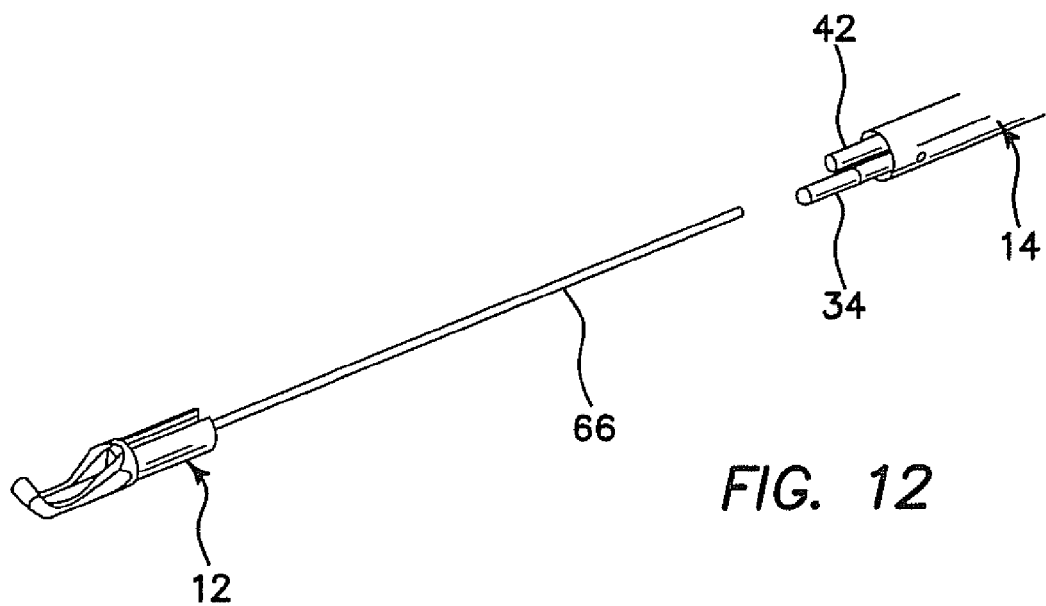
FIG. 12 is an isometric exploded view of the suture cartridge detached from the instrument shaft.

FIG. 12 is an exploded isometric view of the suture cartridge 12 detached from the instrument shaft 14. The tubular structure on the proximal end of the suture cartridge 12 is a suture tube 66. The suture tube 66 houses the suture 44 protruding out of the proximal end of the suture cartridge 12. The suture tube 66 allows for enough room for an adequate amount of suture necessary for one plication stitch. The suture tube 66 is the first part of the suture cartridge 12 that gets inserted into the instrument shaft 14. An attachment mechanism locks the suture cartridge to the instrument shaft. The suture cartridge can also be detached from the instrument shaft when the plication stitch is complete and a new suture cartridge needs to be re-loaded.

Figure 13:
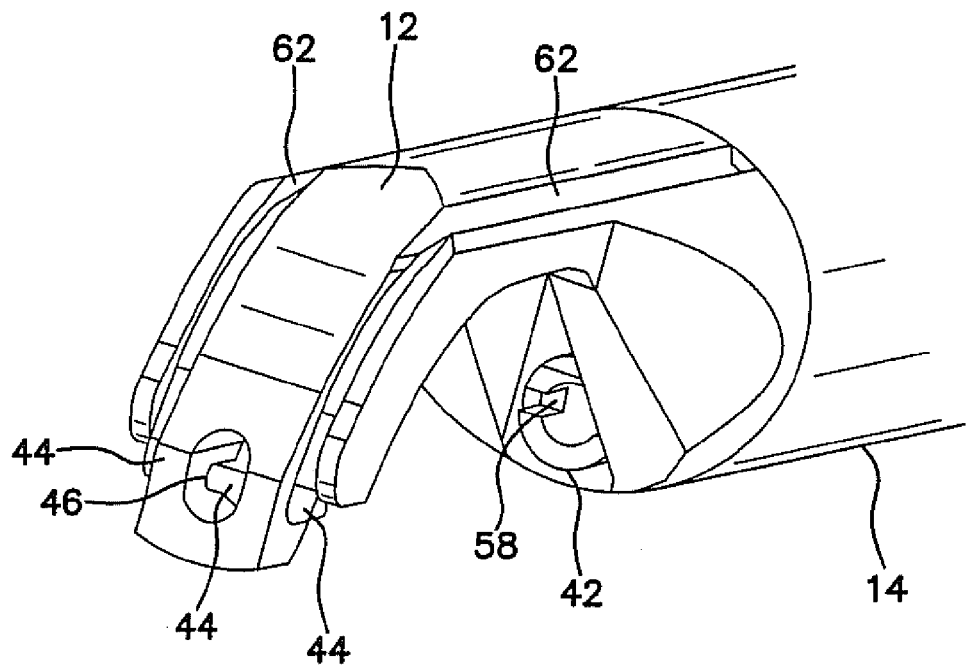
FIG. 13 is an isometric view of the suture cartridge and the distal end of the instrument of the invention.

In FIG. 13 there is shown an isometric view of the suture cartridge 12 and the distal end of the instrument. The suture 44 can be seen running along the suture path grooves 62 of the suture cartridge 12 and through the suture pick-up feature 46. The suture path grooves 62 can have varying widths to control the friction generated by the suture running through the grooves. Friction can be used to keep the suture 44 from falling out of the suture path grooves 62, but must be controlled to minimize the needle retraction forces. Also seen is the hole of the suture pick-up feature, that allows the needle to pass, but maintains the position of the suture on the suture pick-up feature 46.

Figure 14:
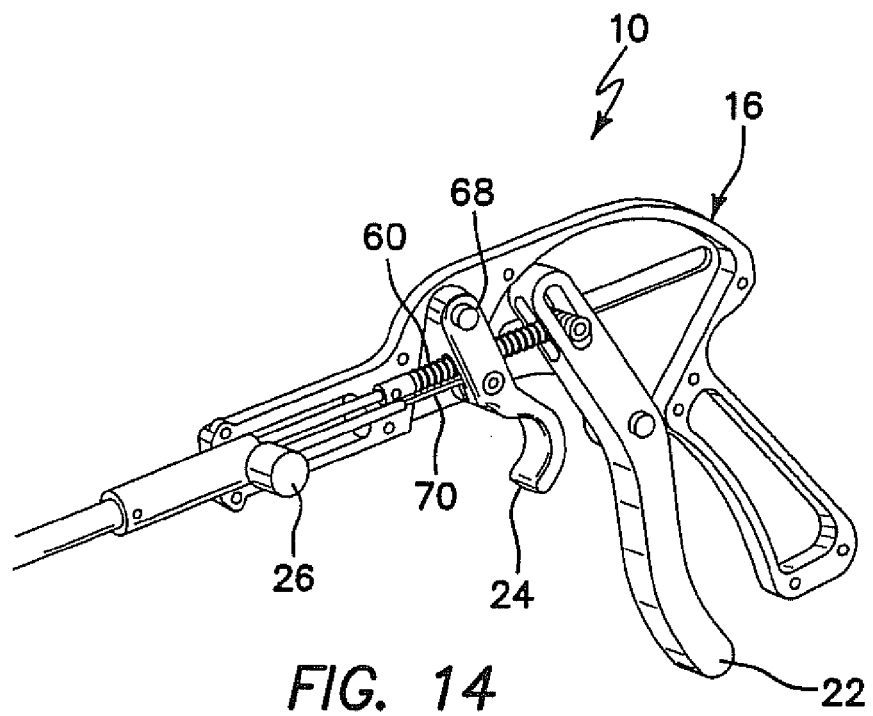
FIG. 14 is an isometric view of the handle portion of the instrument with the handle cover removed for visibility.

FIG. 14 illustrates, in greater detail, the handle portion 16 of the inventive instrument 10, with the housing 18 removed for visibility. By rotationally loosening the shaft advancement knob 26, the surgeon can retract or advance the shaft 14. Once the desired position is achieved, the shaft advancement knob 26 is tightened to maintain position. The grasper actuation trigger 24 pivots on a pin 68 inside the handle and is connected to the flexible cable grasper 34 via a pull wire 70.

Pulling the trigger 24 proximally closes the grasper jaws 36, 38, and pushing the trigger distally opens the jaws. The needle advancement lever 22 is linked to the needle 40. Actuating the needle advancement lever 22 proximally advances the needle 40 and the needle support tube 42, as discussed above. Positioned coaxially over the needle 40 is the needle return spring 60. On the distal end of the needle return spring 60 there is a hub of the needle support tube 42 which provides a hard stop for the needle return spring 60. This needle support tube hub travels with the needle during advancement until a hard stop on the handle is reached. Once the hard stop is reached, the needle continues to advance, but the needle support tube does not. This causes the needle return spring to be compressed. This compression aids the retraction of the suture-loaded needle through the pleated capsular tissue 48.

Now with reference to FIGS. 15-27, a second, modified embodiment of the invention is illustrated, wherein like elements to those in the embodiment of FIGS. 1-14 are designated by like reference numerals, preceded by the numeral 1.

Figure 15:
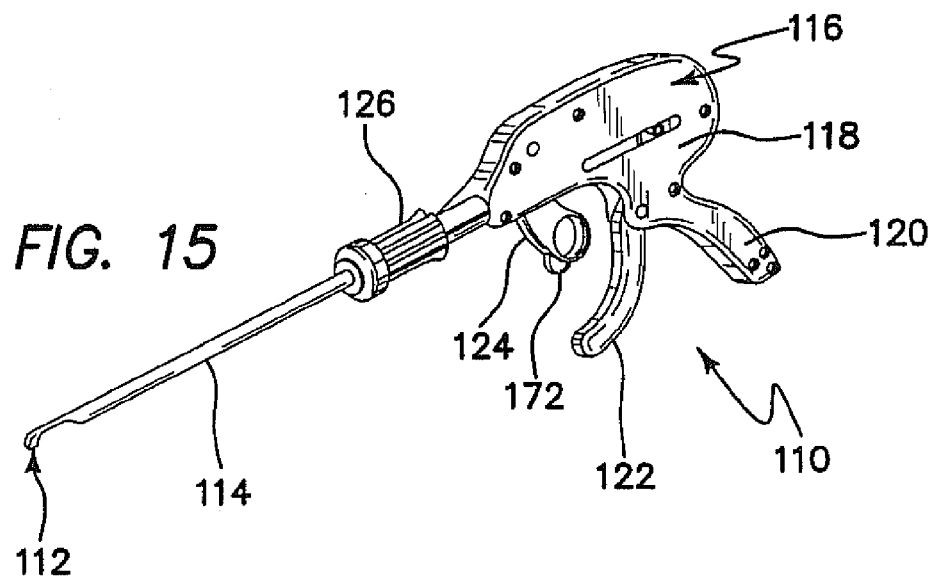
FIG. 15 is a perspective view of a plication instrument constructed in accordance with a second embodiment of the present invention.

Thus, in FIG. 15, there is shown a modified plication instrument 110, having a suture cartridge 112, an instrument shaft 114, and a handle portion 116. The shaft 114 is integrated into the proximal handle portion 116, which comprises a handle housing 118. The attachment of the suture cartridge 112 to the instrument shaft 114 allows the practitioner to unload and re-load suture cartridges 112 after every plication stitch. Extending from the handle housing 118 are a grip 120, a needle advancement lever 122, and a grasper actuation trigger 124. Shaft advancement knob 126 is provided on the shaft 114.

Figure 16:
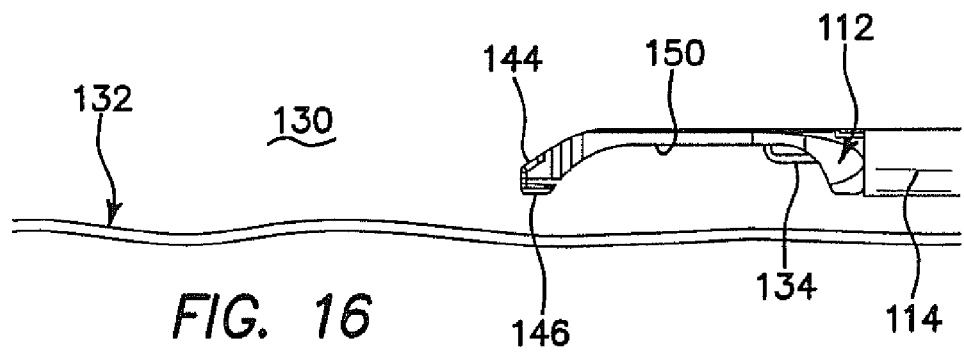
FIG. 16 is a side view of the distal working end of the instrument shown in FIG. 15, wherein the instrument has been introduced into an operative site.
Figure 17:
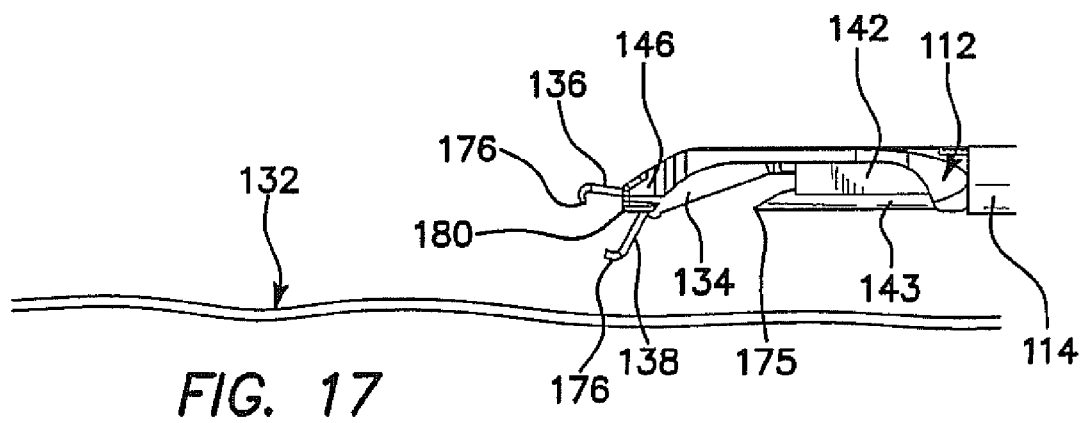
FIG. 17 is a side view similar to FIG. 16, wherein the instrument shaft is in a retracted position so that the graspers have exited the instrument.

Now with reference to FIGS. 16-27, as well as FIG. 15, in FIG. 16 the instrument 110 has been advanced into the operative site 130, which is preferably a human shoulder, approaching the shoulder capsule 132. A flexible cable grasper 134 is housed inside the instrument shaft 114 and is axially fixed to the proximal handle 116. The flexible cable grasper 134 comprises a hinged upper jaw 136 and a hinged lower jaw 138 (FIG. 17).

Opening and closing of the flexible cable grasper jaws 136, 138 is actuated by the grasper actuation trigger 124. The grasper 134 can also maintain a locked, closed jaw position by actuating the trigger 124 to its furthest proximal position until a snap is engaged. This snap can be engaged by actuating a grasper unlock button 172. This locking feature enables the practitioner to release the trigger 124 and to focus on suture passing once the target shoulder capsule 11 location is grasped and locked. Advancing and retracting the instrument shaft 114 is accomplished by actuating the shaft advancement knob 126. Retracting the instrument shaft 114 exposes the grasper 134 outside of the instrument and enables the instrument to be used as a grasper. Advancing the instrument shaft 114 brings the grasper 134 inside the instrument, enabling the instrument to be used as a suture passer. Various instrument shaft positions allow various sized plication pleats to be achieved.

The flexible cable grasper 134 has a flexible shaft on the distal end thereof to permit it to maneuver in and out of the instrument during the instrument shaft 114 advancement and retraction operations. The suture cartridge 112 includes a redirecting curve, as in the embodiment of FIGS. 1-14, for guiding the flexible cable grasper 134 out of the instrument as the instrument shaft 114 is retracted. Housed inside the handle portion 116 is the proximal portion of a suture passing system, which comprises a needle 140, a sharpened needle support tube 143, and a needle return spring (not shown).

Again referring to FIG. 16, as mentioned above, the instrument 110 is disposed at an operative site 130, preferably inside a human shoulder, approaching the shoulder capsule 132. The flexible cable grasper 134 is positioned inside the instrument, maintaining a low profile which facilitates easy insertion of the instrument into the cannula typically used during arthroscopic shoulder repair surgery. The needle 140, the blunt needle support tube 142, and the sharpened needle support tube 143 are in a retracted position at this juncture, in anticipation of the grasper 134 exiting the instrument, and thus not shown in FIG. 16. The suture 144 is loaded onto the suture cartridge 112, and is ready to be hooked onto the needle at the suture pick-up feature 146 of the suture cartridge 112.

FIG. 17 is a side view showing the instrument shaft 114 in a retracted position which results in the graspers 134 exiting the instrument. In this position, the instrument can be used as a grasper. The practitioner is to grasp the capsule 132 in the target location in which the suture entrance point 174 (FIG. 19) is desired. The grasper reaches the target capsule tissue 132 and attempts to grasp the tissue. The grasper jaws 136, 138, each having a rat-tooth feature 176, are in the open position, as illustrated.

Figure 18:
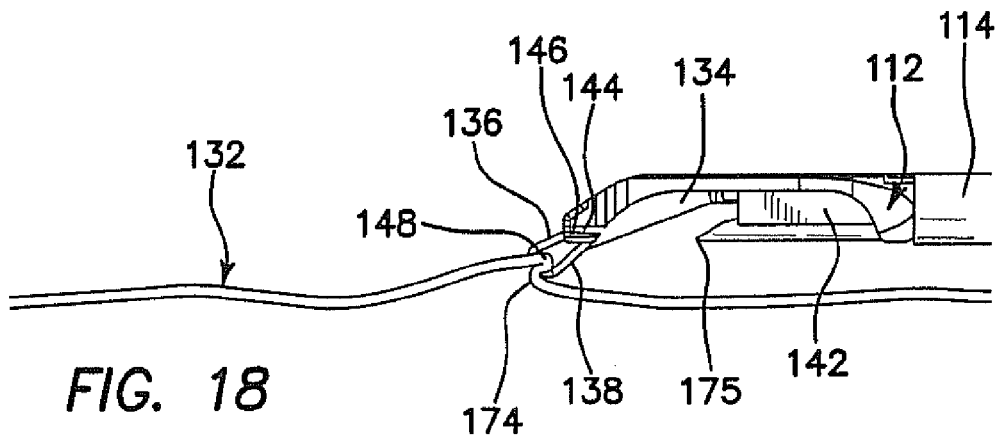
FIG. 18 is a side view similar to FIG. 17, showing the grasper holding the capsule tissue.

In FIG. 18, the grasper 134 has been further advanced, and is holding a portion 148 of the capsule tissue 132. The grasper actuation trigger 124 is in the locked position, maintaining hold of the capsule tissue portion 148. If the practitioner decides that another suture entrance point 174 is more optimal, the grasper unlock button 172 can be actuated, the grasper 134 can release the capsule tissue portion 148, and another target suture entrance point 174 can be grasped. The needle 40 and the sharpened needle support tube 42 are still in the retracted position waiting for the instrument shaft 114 to be advanced and positioned properly such that the distal tip of the instrument is in the target suture exit location 178.

Figure 19:
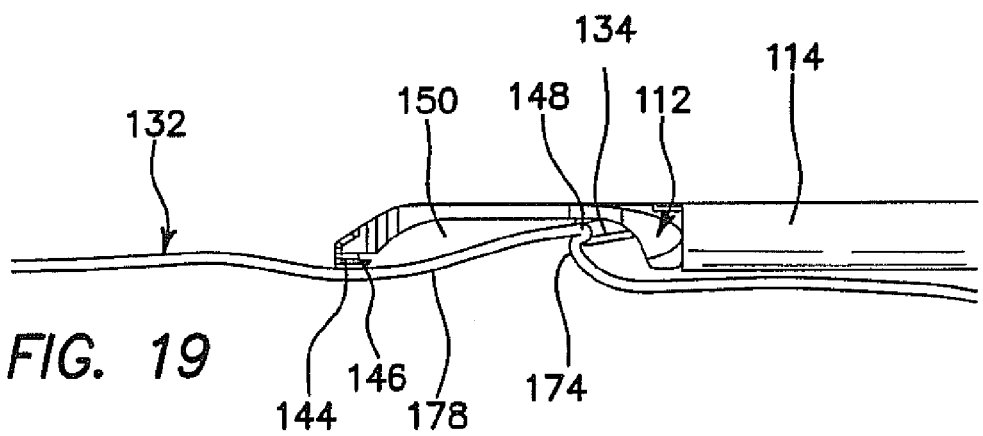
FIG. 19 is a side view similar to FIG. 18, showing the instrument shaft in an advanced position, so that the capsule tissue is positioned for plication.

FIG. 19 shows the instrument shaft 114 in an advanced position. The practitioner has positioned the distal tip of the instrument 110 in the target suture exit location 178. Because the cannula can be pivoted to allow different positional angles and the shaft 114 has advancement and retraction adjustability, the practitioner benefits from a large degree of control for placement of the suture exit location 178. The capsule tissue 132 is now positioned within a tissue bowl 150 for plication. In other words, it is in the direct path of the needle 140 and the sharpened needle support tube 143.

Figure 20:
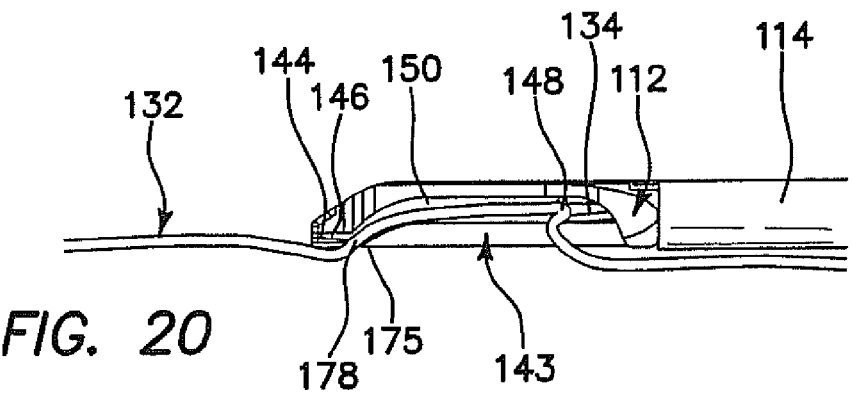
FIG. 20 is a side view similar to FIG. 19, showing the sharpened needle support tube piercing the capsule tissue and traveling underneath the capsule.

In FIG. 20, the sharpened needle support tube 143 is piercing the capsule tissue 132 and traveling beneath the capsule 132. This is important to note, because without this sharpened needle support tube piercing tip 151, the blunt support tube 142, when advanced, would create a pleat prior to advancing the needle. Plication can still be achieved in this manner, but because the instrument is required to create a pleat, it must overcome the tension forces that exist in the capsule tissue 132. By creating this pleat, capsular volume is also reduced prior to plicating. With the sharpened needle support tube 143 as shown, the instrument is no longer required to create a pleat, and therefore does not have to overcome the tensile forces of the capsule tissue, and does not have to reduce the capsular volume prior to plication. The instrument simply passes suture from one point on the capsule to another point on the capsule.

Advantageously, the present invention may be optimized for passing tissue through various types of soft tissue. For example, for particularly pliable tissue, a pleat can be created by positioning the captured tissue into the tissue receiving bowl or cavity 150 and advancing the blunt-tipped needle support tube 142 to contact the tissue prior to piercing the tissue with the hooked needle. On the other hand, for tissue with tension upon it, that is not so pliable, the sharpened needle support tube 143 can penetrate the captured sheet of tissue prior to advancing the hooked needle. This method does not produce a pleat prior to passing the suture therethrough, and thus does no require the suture passing system to overcome the tissue tension created by the pleat.

FIG. 20 shows the grasper 134 maintaining a hold on the capsule tissue portion 148 during this operation by means of several inventive features. One feature is the aforementioned grasper actuation trigger 124 which locks the jaws in the closed position. A second feature is a tensile spring in the grasper drive system which maintains an adequate jaw closure force when the grasper is locked in the closed position. Still another feature is the aforementioned rat-tooth feature 176 of the grasper which creates an interference lock on the captured tissue. The loads required to maintain a grip on the capsule tissue is also minimized by the sharpened needle support tube piercing tip 151 feature. The sharpened needle support tube piercing tip 151 is a standard hypodermic needle point consisting of a triple beveled ground feature commonly used in hypodermic needles. This sharp point enables the piercing loads to be low, which is directly related to the load the grasper must maintain during suture passing. The grasper further contributes to the ease of the sharpened needle support tube 143 piercing the capsule 132 by applying the necessary tension to the capsule. The capsule is anatomically attached to the body at one point and the other point is held by the grasper. Holding the capsule tissue in this fashion permits tension to be applied to it, which eases the process of piercing through it with the sharpened needle support tube 143. FIG. 20 shows the sharpened needle support tube 151 in its full distal position. A small gap is shown between the sharpened needle support tube 143 and the suture cartridge 112, which allows space for the second layer of the capsule. The needle advancement lever 122 is not fully actuated at this point, but rather partially actuated. Continuing to advance the needle advancement lever 122 will advance the needle, piercing the second layer of the capsule toward the suture pick-up feature 146.

Figure 21:
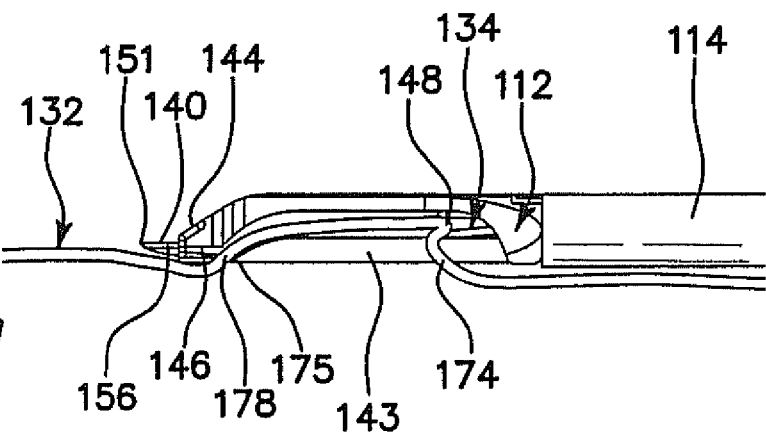
FIG. 21 is a side view similar to FIG. 20 showing the needle in its fully actuated position at the suture pick-up feature of the inventive device

FIG. 21 shows the needle 140 in its fully actuated position at the suture pick-up feature 146. In this position, the needle advancement lever 122 is also in its fully actuated position. As the needle advancement lever 122 is advanced to this position, the needle 140 has also advanced and pierced the second layer of the capsule 132 at the target suture exit point 178. The needle also has a triple bevel ground tip commonly used in hypodermic needles which allows it to pierce through the capsule easily. Also, because the needle is aligned with the suture pick-up feature 146, the suture cartridge 112 provides a back stop which applies the necessary opposing force to pierce through the capsule as the needle is advanced. After the needle pierces the tissue and is fully advanced, it captures the suture 144 and is retracted back through the tissue, bringing along with it the suture 144. To reduce the force required to retrieve the suture loaded needle back through the tissue, the needle suture channels 156 provide relief space for the suture 144. With the suture 144 in the needle suture channels 156, the profile of the suture loaded needle is reduced, which in turn reduces the force required to bring it back through the tissue. Another component that assists this maneuver is the needle return spring located in the proximal handle portion 116. This spring is compressed when the needle is fully advanced, thus creating a return force for the needle to return back through the tissue and back into the sharpened needle support tube 143.

Figure 22:
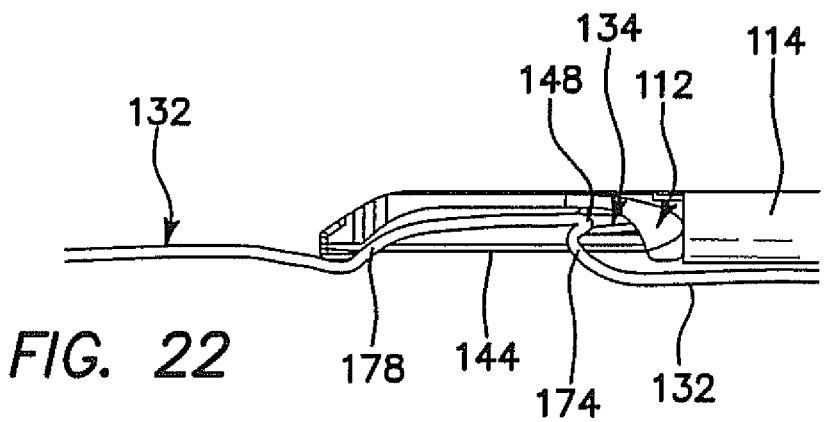
FIG. 22 is a side view similar to FIG. 21 showing the suture having been passed through the capsule tissue.

FIG. 22 shows the suture 144 having been passed through the capsule tissue 132. The grasper 134 is still holding the capsule tissue portion 148 and the sharpened needle support tube 143 and the needle 140 have both been retracted but are still retaining one end of the suture 144. The needle return spring in the handle is still compressed, thereby imposing a retraction load on the needle 140 into the sharpened needle support tube 143. Because of this loading condition, and because the suture 144 is captured by the hook of the needle 140, this suture end is locked to the suture passing system. The other free end of the suture is housed in the suture cartridge 112. At this point, the grasper unlock button 172 can be actuated, causing the grasper to release the captured tissue portion 148 without any type of instrument shaft motion.

Figure 23:
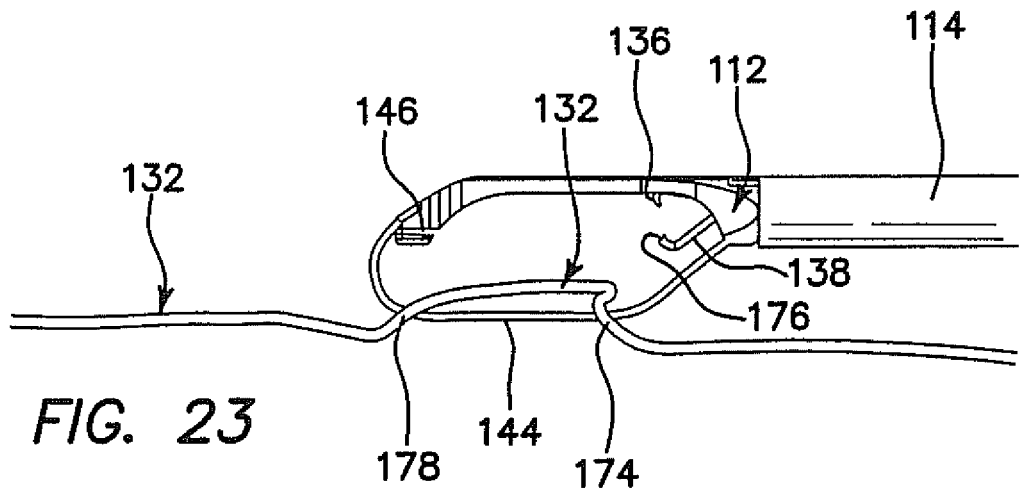
FIG. 23 is a side view similar to FIG. 22, showing the capsule completely released from the grasper, wherein the instrument is being retracted out of the shoulder.

In FIG. 23, the captured tissue portion 148 has been completely released by the grasper jaws 136, 138, and the instrument 110 is in the process of being retracted out of the shoulder site 130. One end of the suture 144 is captured by the suture passing system, as discussed above, while the other suture end is free and is being dispensed out of the suture cartridge 112.

Figure 24:
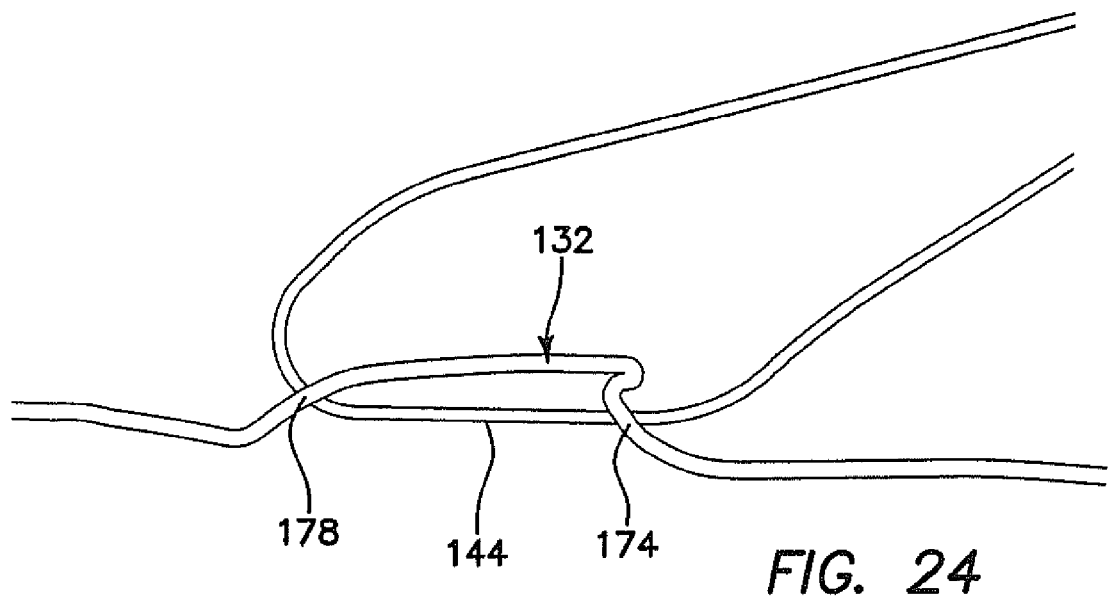
FIG. 24 is a side view showing the end result of the instrument maneuvers in accordance with methods of the invention, wherein the suture has been passed through the target suture entrance point and the target suture exit point.

FIG. 24 shows the end of the instrument maneuvers, which constitute part of the inventive method. As shown, the suture 144 has been passed through the target suture entrance point 174 and the target suture exit point 178. The instrument enables the practitioner to have control of both the suture entrance and suture exit locations. Another benefit that is derived from this is the ability to control the plication length. Because of the shaft position adjustability, the practitioner has the ability to create various sizes of plications. The next procedural step for the practitioner is to throw the appropriate standard knots and cinching the pleat, resulting in plicated capsule tissue.

Figure 25:
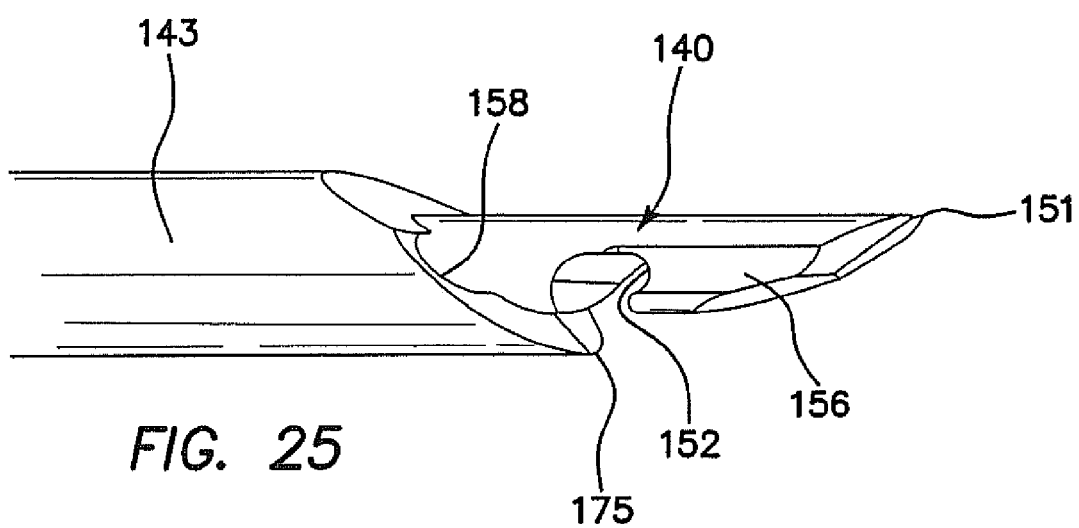
FIG. 25 is an isometric view of the distal end of the needle and the sharpened needle support tube of the inventive device.

FIG. 25 is a close-up isometric view of the distal end of the needle 140 and the sharpened needle support tube 143. The very distal tip 151 consists of a triple bevel geometry, commonly used in hypodermic needles for piercing tissue. A suture hook 152 is the feature that captures the suture 144 during the needle retraction maneuver. The large opening on the proximal side of the hook 152 allows the suture 144 to slide in easily, and the overhang feature maintains the suture inside the hook, capturing it while the needle is retracted. On both sides of the needle 140, suture channels 156 are cut into the needle 140 to provide relief space for the suture 144 during the needle retraction maneuver. The suture relief groove 158 in the sharpened needle support tube also aids the needle retraction maneuver by providing a relief space for the suture on the proximal side of the tissue. This prevents the tissue from getting caught between the suture and the needle support tube, which could result in high needle retraction forces or suture shearing. The sharpened needle support tube 143 provides several functions. As the needle advancement lever 122 is actuated, the sharpened needle support tube 143 pierces the first layer of the capsule 132 and travels beneath the capsule. The sharpened needle support tube 143 piercing tip 175 is comprised of a ground triple bevel geometry commonly used in hypodermic needles. This proven geometry allows for easy piercing of the capsule 132. Furthermore, the orientation angle of the sharpened needle support tube piercing tip 175 enables it to dissect through the tissue plane while traveling beneath the capsule 132. Orienting it in the opposite way may allow for the sharpened needle support tube to provide structural support and to maintain alignment of the needle 140 to the suture pick-up feature 146. During the needle piercing maneuver, lateral loads may be imposed on the needle 140 which may cause the needle 140 to flex and misalign from the suture pick-up feature 146. The sharpened needle support tube 143 extends out from the suture cartridge 112 minimizing the unsupported length of the needle 140. Another function of the needle support tube 143 is to provide an opposing force against the tissue 132 during the needle retraction maneuver.

Figure 26:
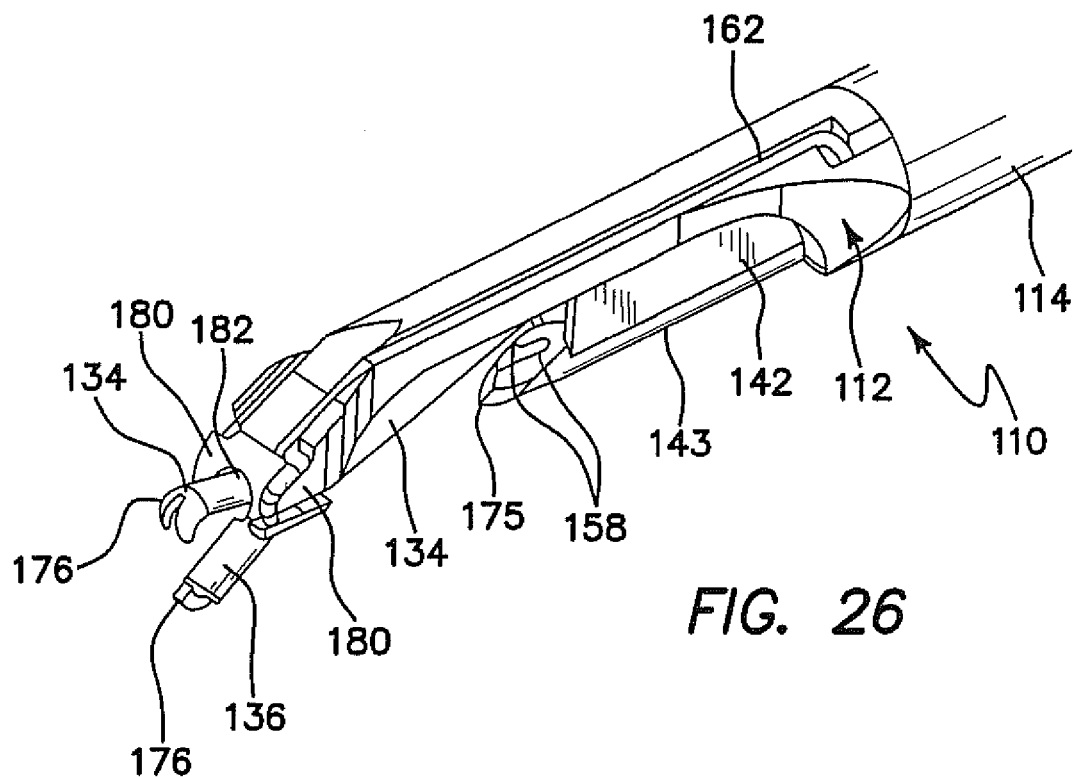
FIG. 26 is an isometric view of the distal end of the inventive instrument, wherein the shaft is positioned such that the graspers are exposed.

Now with respect to FIG. 26, there is shown an isometric view of the distal end of the instrument 110. The instrument shaft 114 is positioned such that the graspers 134 are exposed. The graspers benefit from grasper lateral supports 180, which are features on the suture cartridge 112. A track travels along the inside of the suture cartridge 112 which guides the grasper as it exits out of the instrument. The end of this track results in a U-shaped groove 182. The sides of this U-shaped groove 182 are the grasper lateral supports 180. The instrument shaft 114, when fully retracted, positions the grasper 134 in the position shown, which allows for full opening and closing of the grasper jaws 136, 138. The grasper lateral supports 180 provide structural support to the grasper 134. These supports provide the necessary strength to oppose the loads during instrument operation and maneuvering. The U-shaped groove 182 also maintains a low instrument profile even when the graspers are exposed. Also shown in FIG. 26 is the rat-tooth feature 176 of the grasper 134. This is a standard jaw configuration for graspers when tissue grasping and maintaining a grip on the target tissue is the end goal. Two sharp teeth are on the top jaw 136 and one sharp tooth is on the bottom jaw 138. When the jaws are closed, the teeth mate with each other, causing an interference type of clamping when tissue is grasped.

Figure 27:
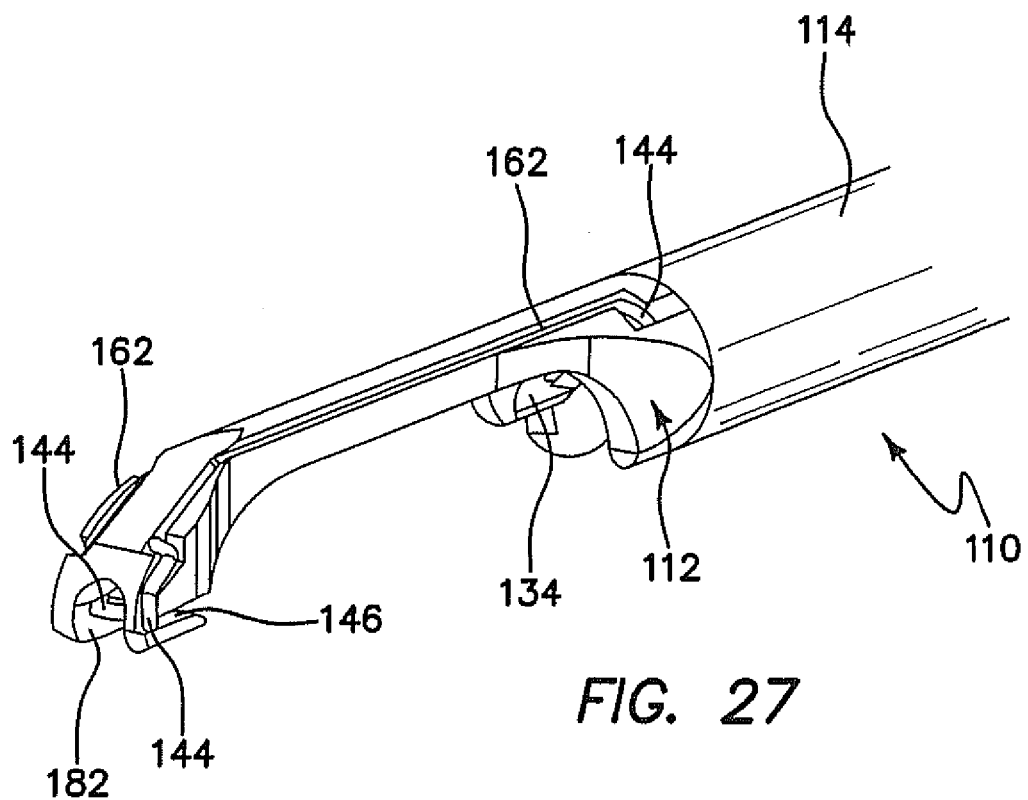
FIG. 27 is an isometric view, similar to FIG. 26, showing the suture running along the suture path grooves and through the suture pick-up feature.

FIG. 27 is a close-up isometric view of the suture cartridge 112 and the distal end of the instrument 110. The suture 144 can be seen running along the suture path grooves 162 of the suture cartridge 112 and through the suture pick-up feature 146. The suture path grooves 162 can have varying widths to control the friction of the suture 144. Friction can be used to keep the suture 144 from falling out of the suture path grooves 162, but must be controlled to minimize the needle retraction forces. Also depicted is the U-shaped groove 182 and the suture pick-up feature 146 that allows the needle to pass, but maintains the position of the suture on the suture pick-up feature.

It is to be understood that the figures of the bone and anchors seen above are purely illustrative in nature, and are not intended to perfectly reproduce the physiologic and anatomic nature of the humeral head as expected to be seen in the human species, nor to limit the application of the inventive embodiments to repair of the rotator cuff. The invention is applicable to many different types of procedures involving, in particular, the attachment of connective or soft tissue to bone. All of the terms used herein are descriptive rather than limiting, and many changes, modifications, and substitutions may be made by one having ordinary skill in the art without departing from the spirit and scope of the invention, which is to be limited only in accordance with the following claims.

What is claimed is:

1. A system for transdermal repair of soft tissue, said system including an instrument comprising:

an instrument shaft having an axis;

a flexible cable grasper disposed within said instrument shaft and being capable of advancing and retracting in a generally axial direction;

a suture source disposed on the distal side of said instrument, and comprising a suture cartridge having a length of suture pre-loaded thereon, said suture cartridge being separate and apart from said flexible cable grasper and comprising the sole source of suture for said instrument, such that no suture originates from any source apart from said suture cartridge, and said instrument shaft extending proximally from said suture cartridge, wherein said suture cartridge comprises a redirecting curve portion with a curved surface that is structured and configured to guide said flexible cable grasper outside of said instrument as said instrument shaft is retracted;

a needle disposed within said instrument shaft which is capable of advancing and retracting in a generally axial direction; and a needle support tube which is capable of advancing and retracting in coordination with said needle in a generally axial direction.

2. The system as recited in claim 1, wherein said flexible cable grasper comprises a flexible cable having a plurality of hinged jaws capable of articulation between closed and opened orientations on a distal end thereof.

3. The system as recited in claim 2, and further comprising a controller on a proximal portion of said instrument for opening and closing said hinged jaws.

4. The system as recited in claim 3, and further comprising a locking mechanism for locking said grasper in one of a closed and opened orientation.

5. The system as recited in claim 1, and further comprising a controller on a proximal portion of said instrument for selectively advancing and retracting said instrument shaft.

6. The system as recited in claim 5, wherein said instrument shaft may be selectively advanced to various distal positions in order to select a desired plication length.

7. The system as recited in claim 6, wherein said instrument shaft may be locked into a desired advanced distal position.

8. The system as recited in claim 1, and further comprising a controller on a proximal portion of said instrument for advancing and retracting said needle.

9. The system as recited in claim 1, and further comprising a suture pick-up feature disposed at a distal end of said instrument, said suture pick-up feature having disposed thereon a portion of a length of suture.

10. The system as recited in claim 9, and further comprising a suture hook on a distal end of said needle, for engaging and retaining said portion of a length of suture as the needle is advanced to said suture pick-up feature.

11. The system as recited in claim 1, wherein said grasper is adapted to capture a desired portion of soft tissue and to withdraw said captured portion of tissue proximally to a desired location.

12. The system as recited in claim 11, wherein said desired location is in a pathway of said needle as said needle is advanced or retracted.

13. The system as recited in claim 1, wherein said suture cartridge is re-loadable or replaceable.

14. The system as recited in claim 1 and further comprising a suture relief groove and a suture path groove for providing relief space for the suture and for reducing loading forces on said needle as it passes through tissue.

15. The system as recited in claim 1, wherein said needle support tube has a sharpened distal tip.

16. The system as recited in claim 15, and further comprising a second needle support tube having a blunt distal tip.

17. The system as recited in claim 16, wherein either of said sharpened or blunt needle support tubes may be selectively advanced to contact a portion of soft tissue captured by said instrument prior to advancement of said needle through said portion of tissue.

* * * * *